United States Patent [19]

Sweeney

[11] 4,431,826

[45] Feb. 14, 1984

[54] PROCESS FOR THE PREPARATION OF ALKENYL SUCCINIC ANHYDRIDE

[75] Inventor: William A. Sweeney, Larkspur, Calif.

[73] Assignee: Chevron Research Company, San Francisco, Calif.

[21] Appl. No.: 410,113

[22] Filed: Aug. 20, 1982

[51] Int. Cl.$^3$ .............................................. C07D 307/60
[52] U.S. Cl. ..................................... 549/255; 162/158
[58] Field of Search .......................... 549/255; 162/158

[56] References Cited

U.S. PATENT DOCUMENTS 3,102,064  8/1963  Wurzburg et al. ................... 549/255
3,821,069  6/1974  Wurzburg ............................ 162/158
4,046,900  8/1977  Mazzarella et al. ................. 162/158

*Primary Examiner*—Henry R. Jiles
*Assistant Examiner*—Bernard Dentz
*Attorney, Agent, or Firm*—D. A. Newell; T. G. De Jonghe; C. J. Caroli

[57] ABSTRACT

An improved process for the preparation of alkenyl succinic anhydride from maleic anhydride and a mixture of straight chain alpha olefins in the $C_{13}$ to $C_{22}$ range which comprises separating the alpha olefins into a lower boiling fraction and a higher boiling fraction, isomerizing the higher boiling fraction, recombining the two fractions and reacting them with maleic anhydride.

12 Claims, No Drawings

PROCESS FOR THE PREPARATION OF ALKENYL SUCCINIC ANHYDRIDE

BACKGROUND OF THE INVENTION

This invention relates to an improved process for the preparation of alkenyl succinic anhydride.

It is known in the art that long straight chain alkenyl succinic anhydrides can be used as effective paper sizing agents. See, for example, U.S. Pat. Nos. 3,102,064; 3,821,069; 3,968,005; and 4,040,900 (Re. 29,960). These alkenyl succinic anhydrides have also been used as fabric treating agents. See U.S. Pat. No. 2,903,382. The useful molecular weight range of the alkenyl group on these sizing agents has variously been described as encompassing 8 to 35 carbon atoms.

It is also known that these prior art sizing agents are best applied in a highly dispersed form, such as an aqueous emulsion. However, alkenyl succinic anhydrides made from straight chain alpha olefins are solids at ambient temperatures and are therefore not effective in forming these emulsions. In view of this, many commercial alkenyl succinic anhydride paper sizing agents are made from isomerized straight chain alpha olefins (i.e., straight chain internal olefins) or from branched chain olefins. See, for example, the frequent reference to "isooctadecenyl succinic anhydride" in U.S. Pat. No. 3,102,064.

It has been taught that the molecular weight of the alkenyl group of the more effective or preferred alkenyl succinic anhydride sizing agents corresponds to a carbon number in the 13 to 22 carbon atom range. Mixtures of several carbon numbers have also been described. See, for example, the reference to $C_{15-20}$ alkenyl succinic anhydride in U.S. Pat. No. 4,040,900 (Re. 29,960).

SUMMARY OF THE INVENTION

The present invention provides an improved process for the preparation of alkenyl succinic anhydride from maleic anhydride and a mixture of straight chain alpha olefins in the $C_{13}$ to $C_{22}$ range which comprises:

(A) introducing the alpha olefins into a distillation zone wherein at least a portion of the lowest boiling alpha olefin is vaporized and taken overhead;

(B) isomerizing the remaining bottoms from the distillation zone to reduce the alpha olefin content to less than 15% of the total olefin bottoms content;

(C) recombining the alpha olefin overhead fraction recovered from step (A) with the isomerized olefin bottoms fraction of step (B); and (D) reacting the recombined olefins from step (C) with maleic anhydride to provide the alkenyl succinic anhydride product.

In another aspect of the invention, the unisomerized alpha olefin overhead fraction recovered from step (A) and the isomerized olefin bottoms fraction of step (B) are each independently reacted with maleic anhydride, and the resulting alkenyl succinic anhydride products are then combined to provide the alkenyl succinic anhydride of the invention.

Preferably, the alpha olefin content in step (B) is reduced to less than 10%, and more preferably, less than 5%, of the total olefin bottoms content.

The alkenyl succinic anhydride prepared by the present process is a two-component alkenyl succinic anhydride composition with superior paper sizing properties which comprises:

(A) the reaction product of maleic anhydride and straight chain alpha olefins in the $C_{13}$ to $C_{18}$ range having an average molecular weight of from about 182 to 238; and (B) the reaction product of maleic anhydride and straight chain internal olefins in the $C_{14}$ to $C_{22}$ range having an average molecular weight of from about 224 to 308;

wherein component (B) has a molecular weight at least 10 units higher than component (A).

Preferably the above mixture contains about 5 to 40% of component (A) and, more preferably, about 10 to 35% of component (A).

Among other factors, the present invention is based on my surprising discovery that certain straight chain alpha olefin-derived alkenyl succinic anhydrides, heretofore considered not useful, can be combined in specific mixtures with other alkenyl succinic anhydrides to provide a superior paper sizing product.

An additional advantage of the present invention is the fact that, when straight chain alpha olefins are being used as the starting feedstock for making liquid alkenyl succinic anhydrides, less olefin processing is required prior to forming the alkenyl succinic anhydride.

DETAILED DESCRIPTION OF THE INVENTION

The composition of the present invention may be prepared by simply combining the described alkenyl succinic anhydride components or, alternatively, by combining the precursor olefins and then making the desired alkenyl succinic anhydride. For example, a broad range straight chain alpha olefin mixture, which may be obtained from wax cracking, Fischer-Tropsch synthesis or ethylene oligomerization, could be distilled to yield light and heavy fractions. The heavy fraction is then isomerized to move the double bond to internal positions and recombined with the light fraction before making the alkenyl succinic anhydride composition of the present invention.

The olefin feed for component (A) of the present composition should be predominantly straight chain 1-olefin. Minor amounts of chain branching or internal olefin, such as is found in commercial "alpha olefins," may also be present.

The olefin feed for either component (A) or (B) may consist of a single carbon number, a mixture of contiguous carbon numbers, or may consist of any combination of carbon numbers within that range.

According to the process of this invention, the olefin feed for component (B) is a straight chain internal olefin obtained by isomerizing straight chain alpha olefins in the $C_{14}$ to $C_{22}$ range. This isomerization may be accomplished using acidic or basic catalysts. The isomerization should be sufficient to leave no more than about 15% alpha olefin remaining, preferably less than 10%, and more preferably, less than 5% alpha olefin. These olefins may be augmented by the inclusion of branched chain olefins or internal straight chain olefins obtained from other sources. Branched chain olefins may be obtained from various sources, such as by oligomerization of lower olefins in the $C_3$ to $C_{11}$ range. The straight chain internal olefins may be obtained from n-paraffins by processes well known in the art, such as by dehydrogenation or chlorination-dehydrochlorination. In general, the olefin feed for component (B) should be substantially free of straight chain alpha olefin.

The novel sizing agents display all of the features and advantages of the cited prior art sizing agents. Moreover, the novel sizing agents of this invention impart to paper sized therewith a particularly good resistance to acidic liquids such as acid inks, citric acid, lactic acid etc. as compared to paper sized with the sizing agents of the cited prior art. In addition to the properties already mentioned, these sizing agents may also be used in combination with alum as well as with any of the pigments, fillers and other ingredients which may be added to paper. The sizing agents of the present invention may also be used in conjunction with other sizing agents so as to obtain additive sizing effects. A still further advantage in that they do not detract from the strength of the paper and when used with certain adjuncts will, in fact, increase the strength of the finished sheets. Only mild drying or curing conditions are required to develop full sizing value.

The actual use of these sizing agents in the manufacture of paper is subject to a number of variations in technique any of which may be further modified in light of the specific requirements of the practitioner. It is important to emphasize, however, that with all of these procedures, it is most essential to achieve a uniform dispersal of the sizing agent throughout the fiber slurry in the form of minute droplets which can come in intimate contact with the fiber surface. Uniform dispersal may be obtained by adding the sizing agent to the pulp with vigorous agitation or by adding a previously formed, fully dispersed emulsion. Chemical dispersing agents may also be added to the fiber slurry.

Another important factor in the effective utilization of the sizing agents of this invention involves their use in conjunction with a material which is either cationic in nature or is, on the other hand, capable of ionizing or dissociating in such a manner as to produce one or more cations or other positively charged moieties. These cationic agents, as they will be hereinafter referred to, have been found useful as a means for aiding in the retention of sizing agents herein as well as for bringing the latter into close proximity to the pulp fibers. Among the materials which may be employed as cationic agents in the sizing process, one may list alum, aluminum chloride, long chain fatty amines, sodium aluminate, substituted polyacrylamide, chromic sulfate, animal glue, cationic thermosetting resins and polyamide polymers. Of particular interest for use as cationic agents are various cationic starch derivatives including primary, secondary, tertiary or quaternary amine starch derivatives and other cationic nitrogen substituted starch derivatives, as well as cationic sulfonium and phosphonium starch derivatives. Such derivatives may be prepared from all types of starches including corn, tapioca, potato, waxy maize, wheat and rice. Moreover, they may be in their original granule form or they may be converted to pregelatinized, cold water soluble products.

Any of the above noted cationic agents may be added to the stock, i.e., the pulp slurry, either prior to, along with, or after the addition of the sizing agent. However, in order to achieve maximum distribution, it is preferable that the cationic agent be added either subsequent to or in direct combination with the sizing agent. The actual addition to the stock of either the cationic agent or the sizing agent may take place at any point in the paper making process prior to the ultimate conversion of the wet pulp into a dry web or sheet. Thus, for example, these sizing agents may be added to the pulp while the latter is in the headbox, beater, hydropulper or stock sheet.

In order to obtain good sizing, it is desirable that the sizing agents be uniformly dispersed throughout the fiber slurry in as small a particle size as is possible to obtain. One method for accomplishing this is to emulsify the sizing agent prior to its addition to the stock utilizing either mechanical means, such as high speed agitators, mechanical homogenizers, or by the addition of a suitable emulsifying agent. Where possible, it is highly desirable to employ the cationic agent as the emulsifier and this procedure is particularly successful where cationic starch derivatives are utilized. Among the applicable non-cationic emulsifiers which may be used as emulsifying agents for the sizing agents, one may list duch hydrocolloids as ordinary starches, non-cationic starch derivatives, dextrines, carboxymethyl cellulose, gum arabic, gelatin, and polyvinyl alcohol as well as various surfactants. Examples of such surfactants include polyoxyethylene sorbitan trioleate, polyoxyethylene sorbitol hexaoleate, polyoxyethylene sorbitol laurate, and polyoxyethylene sorbitol oleate-laurate. When such non-cationic emulsifiers are used, it is often desirable to separately add a cationic agent to the pulp slurry after the addition to the latter of the emulsified sizing agent. In preparing these emulsions with the use of an emulsifier, the latter is usually first dispersed in water and the sizing agent is then introduced along with vigorous agitation. Alternatively, the emulsification techniques described in U.S. Pat. No. 4,040,900 may be employed.

Further improvements in the water resistance of the paper prepared with these novel sizing agents may be obtained by curing the resulting webs, sheets, or molded products. This curing process involves heating the paper at temperatures in the range of from 80° to 150° C. for periods of from 1 to 60 minutes. However, it should again be noted that post curing is not essential to the successful operation of this invention.

The sizing agents of this invention may, of course, be successfully utilized for the sizing of paper prepared from all types of both cellulosic and combinations of cellulosic with non-cellulosic fibers. The cellulosic fibers which may be used include bleached and unbleached sulfate (kraft), bleached and unbleached sulfite, bleached and unbleached soda, neutral sulfite, semichemical chemiground-wood, ground wood, and any combination of these fibers. These designations refer to wood pulp fibers which have been prepared by means of a variety of processes which are used in the pulp and paper industry. In addition, synthetic fibers of the viscose rayon or regenerated cellulose type can also be used.

All types of pigments and fillers may be added to the paper which is to be sized with the novel sizing agents of this invention. Such materials include clay, talc, titanium dioxide, calcium carbonate, calcium sulfate, and diatomaceous earths. Other additives, including alum, as well as other sizing agents, can also be used with these sizing agents.

With respect to proportions, the sizing agents may be employed in amounts ranging from about 0.05 to about 3.0 percent of the dry weight of the pulp in the finished sheet or web. While amounts in excess of 3% may be used, to benefits of increased sizing properties are usually not economically justified. Within the mentioned range the precise amount of size which is to be used will depend for the most part upon the type of pulp which is being utilized, the specific operating conditions, as well as the particular end use for which the paper is destined. Thus, for example, paper which will require good water resistance or ink holdout will necessitate the use of a higher concentration of sizing agent than paper which does not. The same factors also apply in relation to the amount of cationic agent which may be used in conjunction with these sizing agents. The practitioner will be able to use these materials in any concentration which is found to be applicable to his specific operating conditions. However, under ordinary circumstances a range of from 0.5 to 2.0 parts by weight of cationic agent per 1.0 part of sizing agent is usually adequate. It can be noted that the cationic agent is present in a quantity of at least 0.025 percent of the dry weight of the pulp in the paper.

The alkenyl succinic anhydride compositions of the present invention may also be used to impart water-repellency to cellulosic fabrics.

The water-repellent compositions described above may be applied to the cloth in aqueous emulsions similar to those used for paper sizing. The emulsion may be sprayed onto the fabric or the fabric may be dipped into the emulsion in order to distribute the derivative evenly throughout the fabric. The impregnated fabric is then withdrawn from the solution and air dried. After air drying the cloth is then heated, preferably to a temperature in excess of 100° C., to effect a curing of the impregnated agent within the cloth. It has been found that one may conveniently use a temperature of about 125° C. for a period of 15 to 20 minutes. At lower temperatures longer periods of time are required to effect the curing process. To be commercially practical the curing time should be as short as possible and generally less than one hour. At higher temperatures the heat curing may be accomplished in shorter periods of time. The upper limit of temperature at which the heat curing process may be carried out is limited to the temperatures at which fabrics begin to brown or become discolored. Using the composition of the present invention, it is preferred to impregnate the fabric with from about 0.7 to 2.5% by weight of the fabric of the alkenyl succinic anhydride.

The following examples are provided to illustrate the invention in accordance with the principles of this invention but are not to be construed as limiting the invention in any way except as indicated by the appended claims.

EXAMPLES

Example 1

This example describes the preparation of a standard straight chain alkenyl succinic anhydride suitable for sizing applications.

The feed olefin was derived from cracking petroleum wax and originally contained about 88% straight chain alpha olefin. It consisted of a mixture of homologs from $C_{15}$ to $C_{20}$ containing about 18% $C_{15}$, 19% $C_{16}$, 18% $C_{17}$, 18% $C_{18}$, 15% $C_{19}$ and 12% $C_{20}$. This mixture was isomerized using an acidic catalyst until the alpha olefin content was reduced to 7%. The double bond had been moved to the 2-position and further internal positions.

The above straight chain internal olefin mixture (329 g, 1.35 moles) was heated with maleic anhydride (98 g, 1.0 mole) in an autoclave for 3¼ hours at 230° C. Over 95% of the maleic anhydride reacted with the olefin to give an alkenyl succinic anhydride product. This crude product was stripped of unreacted maleic anhydride and olefin by heating up to 260° C. at 25 mm Hg with nitrogen sparging over a 40-minute period.

The remaining alkenyl succinic anhydride was a straw-colored liquid with a pour point of about 5° C. which remained fluid but formed some solids on standing overnight at this temperature.

This product is very similar to normal commercial straight chain alkenyl succinic anhydride. It gives good paper sizing results in a variety of tests, such as those described in U.S. Pat. No. 4,040,900 (Re. 29,960).

Example 2

An alkenyl succinic anhydride was made as described in Example 1, except that the carbon number range of the feed olefin consisted of 25% $C_{15}$, 30% $C_{16}$, 29% $C_{17}$, and 15% $C_{18}$. The alpha olefin content remaining after isomerization was 7%. The derived alkenyl succinic anhydride was a clear liquid which did not produce solids on standing overnight at 5° C.

Example 3

An alkenyl succinic anhydride was made from the same straight chain alpha olefins as described in Example 1, except that the olefin isomerization step was omitted. The alkenyl succinic anhydride product was a solid, completely unsuitable for sizing by the normal aqueous emulsion techniques.

Example 4

The alpha olefin feed used in Example 1 was distilled to produce a lower boiling fraction which was 88% $C_{15}$ and 9% $C_{16}$, with an average molecular weight of 212. An alkenyl succinic anhydride was made from this olefin using the steps of Example 1 except that the isomerization step was omitted. This alkenyl succinic anhydride was a solid, unsuitable for sizing.

Example 5

An example of the composition of the present invention was made by using the alkenyl succinic anhydride of Example 4 as component A and a $C_{16-18}$ alkenyl succinic anhydride as component B. The $C_{16-18}$ alpha olefin fraction was in the bottoms from distilling out the $C_{15}$ cut of Example 4. This $C_{16-18}$ fraction contained about 34% $C_{16}$, 34% $C_{17}$, and 27% $C_{18}$, with an average molecular weight of 237. The $C_{16-18}$ fraction was isomerized to reduce the alpha olefin content to 7%, and an alkenyl succinic anhydride was made as in Example 1. The final alkenyl succinic anhydride mixture contained 22.5% of component A and 77.5% of component B. This composition was a clear liquid at room temperature. It remained fluid but formed some solids on standing overnight at 5° C.

EXAMPLE 6

Another example of the composition of the present invention was made as described in Example 5, except that the $C_{16-18}$ olefin used to make the alkenyl succinic anhydride of component B was isomerized more completely before reacting with maleic anhydride. In this case, instead of 7% alpha olefin remaining, only 2% alpha olefin remained after isomerizing. This $C_{16-18}$ olefin was reacted with maleic anhydride and the resulting alkenyl succinic anhydride was mixed with the alkenyl succinic anhydride of Example 4 in a 22.5/77.5 ratio as in Example 5. This composition was a liquid at room temperature and did not form any solids on standing overnight at 5° C.

Example 7

Paper sizing experiments and size effectiveness evaluations were run using techniques described in U.S. Pat. No. 4,040,900 (Re. 29,960). For each alkenyl succinic anhydride tested, eight results was obtained. The alkenyl succinic anhydride was added to paper at two different levels: 0.2% and 0.4%, based on dry fiber weight. A cationic starch adjuvant was employed at two times the alkenyl succinic anhydride level, in each case. At both alkenyl succinic anhydride levels, tests were also made with 0.5% added alum. The sized papers were evaluated using both the Hercules size test (80% reflectance end point), and the potassium permanganate test described in U.S. Pat. No. 4,040,900.

For each alkenyl succinic anhydride, the times to obtain each end-point were averaged to give the results shown in Table 1.

TABLE 1

| Alkenyl Succinic Anhydride | | Time, in seconds, to end-point (average of 8 tests) |
|---|---|---|
| Example No. | Carbon Range | |
| 1 | 15–20 | 104 |
| 2 | 15–18 | 110 |
| 5 | 15–18 | 121 |
| 6 | 15–18 | 165 |

The results of Table 1 demonstrate that the alkenyl succinic anhydrides of the present invention, namely Examples 5 and 6, give superior sizing effectiveness compared to the known alkenyl succinic anhydride compositions of Examples 1 and 2.

What is claimed is:

1. A process for the preparation of alkenyl succinic anhydride from maleic anhydride and a mixture of straight chain alpha olefins in the $C_{13}$ to $C_{22}$ range which comprises:
   (A) introducing the alpha olefins into a distillation zone wherein at least a portion of the lowest boiling alpha olefin is vaporized and taken overhead;
   (B) isomerizing the remaining bottoms from the distillation zone to reduce the alpha olefin content to less than 15% of the total olefin bottoms content;
   (C) recombining the alpha olefin overhead fraction recovered from step (A) with the isomerized olefin bottoms fraction of step (B); and
   (D) reacting the recombined olefins from step (C) with maleic anhydride to provide the alkenyl succinic anhydride product.

2. The process of claim 1, wherein the alpha olefin content in step (B) is reduced to less than 10% of the total olefin bottoms content.

3. The process of claim 2, wherein the alpha olefin content in step (B) is reduced to less than 5% of the total olefin bottoms content.

4. The process of claim 1, wherein the amount of olefin taken overhead in step (A) is about 5 to 40% of the total olefin used.

5. The process of claim 4, wherein the amount of olefin taken overhead in step (A) is about 10 to 35% of the total olefin used.

6. The process of claim 1, wherein the average molecular weight of the olefin taken overhead in step (A) is from about 182 to 238 and the average molecular weight of the bottoms olefin in step (B) is from about 224 to 308.

7. A process for the preparation of alkenyl succinic anhydride from maleic anhydride and a mixture of straight chain alpha olefins in the $C_{13}$ to $C_{22}$ range which comprises:
   (A) introducing the alpha olefins into a distillation zone wherein at least a portion of the lowest boiling alpha olefin is vaporized and taken overhead;
   (B) isomerizing the remaining bottoms from the distillation zone to reduce the alpha olefin content to less than 15% of the total olefin bottoms content;
   (C) independently reacting the unisomerized alpha olefin overhead fraction recovered from step (A) and the isomerized olefin bottoms fraction of step (B) with maleic anhydride; and
   (D) combining the reaction products of step (C) to provide the alkenyl succinic anhydride product.

8. The process of claim 7, wherein the alpha olefin content in step (B) is reduced to less than 10% of the total olefin bottoms content.

9. The process of claim 8, wherein the alpha olefin content in step (B) is reduced to less than 5% of the total olefin bottoms content.

10. The process of claim 7, wherein the amount of olefin taken overhead in step (A) is about 5 to 40% of the total olefin used.

11. The process of claim 10, wherein the amount of olefin taken overhead in step (A) is about 10 to 35% of the total olefin used.

12. The process of claim 7, wherein the average molecular weight of the olefin taken overhead in step (A) is from about 182 to 238 and the average molecular weight of the bottoms olefin in step (B) is from about 224 to 308.

* * * * *